United States Patent
Khan et al.

(10) Patent No.: US 12,038,423 B2
(45) Date of Patent: Jul. 16, 2024

(54) PREDICTING INTERNAL CORROSION IN GAS FLOW LINES USING MACHINE LEARNING

(71) Applicant: Saudi Arabian Oil Company, Dhahran (SA)

(72) Inventors: Muhammad Sohaib Khan, Udhailyah (SA); Balakoteswara R. Koppuravuri, Dhahran (SA); Sarafudheen M. Tharayil, Dhahran (SA); Fathi BuGubaia, Mubarraz (SA); Mohammad S. Al-Qahtani, Hasa (SA)

(73) Assignee: Saudi Arabian Oil Company, Dhahran (SA)

( * ) Notice: Subject to any disclaimer, the term of this patent is extended or adjusted under 35 U.S.C. 154(b) by 137 days.

(21) Appl. No.: 17/409,400

(22) Filed: Aug. 23, 2021

(65) Prior Publication Data
US 2023/0057091 A1    Feb. 23, 2023

(51) Int. Cl.
   *G01N 33/00*        (2006.01)
   *G01K 13/024*      (2021.01)
   *G06N 3/02*         (2006.01)

(52) U.S. Cl.
   CPC ....... *G01N 33/0047* (2013.01); *G01K 13/024* (2021.01); *G06N 3/02* (2013.01)

(58) Field of Classification Search
   CPC ..... G01N 33/0047; G01K 13/024; G06N 3/02
   USPC .......................................................... 702/30
   See application file for complete search history.

(56) References Cited

U.S. PATENT DOCUMENTS

| | | | | |
|---|---|---|---|---|
| 11,536,121 | B1* | 12/2022 | Basu | ................ G06N 3/08 |
| 2007/0192078 | A1* | 8/2007 | Nasle | ............. G05B 23/0254 703/14 |
| 2007/0289740 | A1* | 12/2007 | Thigpen | ............. E21B 43/14 166/250.01 |
| 2018/0365555 | A1* | 12/2018 | Aslam | ............ G06N 3/084 |
| 2023/0034897 | A1* | 2/2023 | Silakorn | ........... G05B 23/0283 |

FOREIGN PATENT DOCUMENTS

| | | |
|---|---|---|
| CN | 111412391 | 7/2020 |

OTHER PUBLICATIONS

Masi et al., "A neural network predictive model of pipeline internal corrosion profile," Proceedings of the 2014 First International Conference on Systems Informatics, Modeling and Simulation, Apr. 2014, 6 pages.

* cited by examiner

*Primary Examiner* — Aditya S Bhat
(74) *Attorney, Agent, or Firm* — Fish & Richardson P.C.

(57) ABSTRACT

In an example method, a system obtains first data indicating a plurality of properties of a plurality of gas flow lines. The properties include, for each of the gas flow lines (i) data representing a flow rate of a gas through that gas flow line, (ii) data representing a pressure of the gas in that gas flow line, and (iii) data representing an additive included in the gas in that gas flow line, such as a substance for inhibiting corrosion. For each of the gas flow lines, the system uses a computerized neural network to determine a risk of corrosion associated with that gas flow line based on the properties of that gas flow line, determines whether the metric for that gas flow line is greater than a threshold level, and if so, generates a notification for presentation to a user.

17 Claims, 7 Drawing Sheets

300

310

PREDICTING INTERNAL CORROSION IN GAS FLOW LINES USING MACHINE LEARNING

TECHNICAL FIELD

The disclosure relates to systems and methods for predicting internal corrosion in gas flow lines using machine learning.

BACKGROUND

Gas flow lines can be used to convey gaseous substances from one location to another. As an example, a gas flow line can include one or more pipes, tubes, or other conduits, each having a tubular body with at least one input aperture and at least one outlet aperture. The gas flow line can receive a gaseous substance via one or more of the input apertures, and convey the gaseous substance to one or more of the output apertures via the tubular body.

SUMMARY

Gas flow lines can be used to convey gaseous substances from one location to another. For instance, gas flow lines can be used to convey hydrocarbon gas as a part of a hydrocarbon production and/or distribution process.

Further, gas flow lines may susceptible to internal corrosion. For example, the material of the gas flow line may chemically react with gaseous substances conveyed by the gas flow line and/or the exterior environment, which may weaken the structural integrity of the gas flow line. If the gas flow line becomes sufficiently corroded, one or more holes, gaps, cracks, or other openings may develop on the gas flow line, from which gaseous substances may leak. These leaks may be detrimental to the safety and/or reliability of the gas flow lines.

Machine learning techniques can be used to identify corrosion risks in network of gas flow lines, such that the gas flow lines can be preemptively repaired and/or maintained to avoid or otherwise mitigate the effects of corrosion. For example, a computer system can obtain multiple sets of training data, each set including (i) properties of a respective previously observed gas flow line, and (ii) an indication of the extent of corrosion in that gas flow line (for example, whether that gas flow line has corroded or later become corroded, and if so, the severity of that corrosion). Based on the training data, the computer system can be trained to recognize characteristics of presently observed gas flow lines that are indicative to a corrosion risk, and preemptively warn a user of that corrosion risk.

The implementations described in this disclosure can provide various technical benefits. For instance, the machine learning processes described herein enable a computer system to automatically identify internal corrosion risk in a network of gas flow lines, such that the gas flow line can be preemptively repaired and/or maintained. Accordingly, the network of gas flow lines can be operated in a safer and more reliable manner.

In an aspect, a method includes obtaining, using one or more processors, first data indicating a plurality of first properties of a plurality of first gas flow lines, where the plurality of first properties include, for each of the plurality of first gas flow lines: (i) data representing a flow rate of a gas through that first gas flow line, (ii) data representing a pressure of the gas in that first gas flow line, and (iii) data representing an additive included in the gas in that first gas flow line, where the additive includes a substance for inhibiting corrosion in that first gas flow line. The method also includes, for each of the plurality of first gas flow lines: determining, using the one or more processors implementing a computerized neural network, a risk of corrosion associated with that first gas flow line based on the first properties of that first gas flow line; determining, using the one or more processors, whether the first metric for that first gas flow line is greater than a threshold level; and responsive to determining that the first metric for that first gas flow line is greater than the threshold level, generating, using the one or more processors, a notification indicating the first metric for that first gas flow line for presentation to a user.

Implementations of this aspect can include one or more of the following features.

In some implementations, the plurality of first properties can include, for each of the plurality of first gas flow lines, a composition of the gas in that first gas flow line.

In some implementations, the plurality of first properties can include, for each of the plurality of first gas flow lines, a composition of that first gas flow line.

In some implementations, the method can also include determining that the first data includes data regarding one or more of the plurality of first gas flow lines, and in response, modifying the first data to include additional data regarding the one or more of the plurality of first gas flow lines.

In some implementations, the method can also include determining that the first data includes inaccurate data regarding one or more of the plurality of first gas flow lines, and in response, modifying the first data to correct the inaccurate data regarding the one or more of the plurality of first gas flow lines.

In some implementations, the computerized neural network can be trained based a plurality of sets of training data. Each of the plurality of sets of training data can include second data indicating a plurality of second properties of a plurality of second gas flow lines. The plurality of second properties can include, for each of the plurality of second gas flow lines, data representing a flow rate of a gas through that second gas flow line, data representing a pressure of the gas in that second gas flow line, data representing a second additive included in the gas in that second gas flow line, where the second additive includes a substance for inhibiting corrosion in that second gas flow line, and data representing an extent of corrosion in that second gas line.

In some implementations, the method can also include, for each of the plurality of first gas flow lines, determining a degree of severity of the risk of corrosion associated with that first gas flow line.

In some implementations, the plurality of first gas flow lines can include one or more hydrocarbon gas flow lines.

Other implementations are directed to systems, devices, and devices for performing some or all of the method. Other implementations are directed to one or more non-transitory computer-readable media including one or more sequences of instructions which when executed by one or more processors causes the performance of some or all of the method.

The details of one or more embodiments are set forth in the accompanying drawings and the description. Other features and advantages will be apparent from the description and drawings, and from the claims.

DETAILED DESCRIPTION

Figure 1:
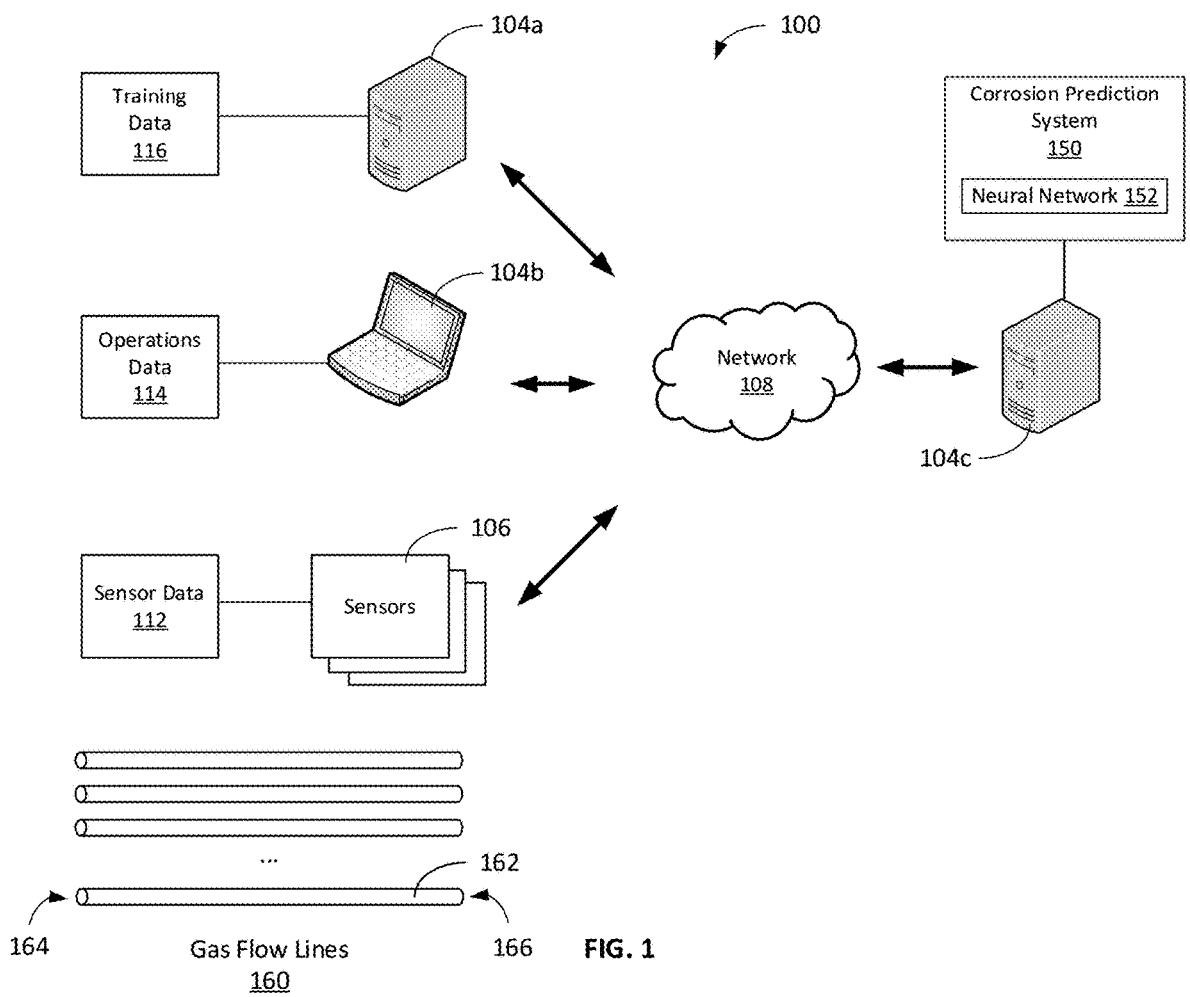
FIG. 1 is a diagram of an example system for predicting corrosion in gas flow lines using machine learning.

FIG. 1 shows an example system 100 for predicting corrosion in one or more gas flow lines 160. The system 100 includes several computer systems 104a-104c and sensors 106 communicatively coupled to one another through a network 108. Further, a corrosion prediction system 150 including a neural network 152 is maintained on at least one of the computer systems (for example, the computer system 104c).

In general, the gas flow lines 160 are configured to convey gaseous substances between two or more locations. As an example, the gas flow lines 160 can convey hydrocarbon gas as a part of a hydrocarbon production and/or distribution process. Example hydrocarbon gases include methane ($CH_4$), ethane ($C_2H_6$), propane ($C_3H_8$), butanes ($C_4H_{10}$), pentanes ($C_5H_{12}$), hexane ($C_6H_{14}$), and heptane ($C_7H_{16}$), among others.

At least some of the gas flow lines 160 can include one or more pipes, tubes, or other conduits for conveying gaseous substances. As an example, a gas flow line 160 can include a tubular body 162 with at least one input aperture 164 and at least one outlet aperture 166. The gas flow line 160 can receive a gaseous substance via one or more of the input apertures 164, and convey the gaseous substance to one or more of the output apertures 164 via the tubular body 162.

Further, at least some of the gas flow lines 160 can be interconnected with one another, such that gaseous substances are conveyed from one or more input apertures of one gas flow line to one or more output apertures of another gas flow line. For example, a network of interconnected gas flow lines 160 can be configured to receive gaseous substances from one or more sources, and convey the gaseous substances to one or more destinations.

In some implementations, at least some of the gas flow lines 160 may susceptible to corrosion. In general, corrosion refers to the process by which a refined metal is converted into a more chemically stable form, such as oxide, hydroxide, carbonate, or sulfide. Corrosion can occur, for example, due to a chemical and/or electrochemical reaction between the material of the gas flow line and the gaseous substances conveyed by the gas flow line. Corrosion can also occur due to a chemical and/or electrochemical reaction between the material of the gas flow line and the exterior environment.

Further, internal corrosion may weaken the structural integrity of the gas flow lines 160. For example, if a gas flow line 160 becomes sufficiently corroded, one or more holes, gasp, cracks, or other openings may develop on the gas flow line 160, from which gaseous substances may leak. These leaks may be detrimental to the safety and/or reliability of the gas flow lines. For example, a gas leak may introduce toxic, reactive, or otherwise dangerous gases into an environment occupied by humans. As another example, a gas leak may reduce the amount of the gaseous substance that is conveyed to a particular destination.

Machine learning techniques can be used to identify internal corrosion risks in the gas flow lines 160, such that the gas flow lines 160 can be preemptively repaired and/or maintained to avoid or otherwise mitigate the effects of corrosion. For example, the corrosion prediction system 150 can obtain multiple sets of training data, each set including (i) properties of a respective previously observed gas flow line, and (ii) an indication of the extent of corrosion in that gas flow line (for example, whether that gas flow line has corroded or later become corroded, and if so, the severity of that corrosion). Based on the training data, the corrosion prediction system 150 can train a neural network 152 to recognize characteristics of presently observed gas flow lines that are indicative to a corrosion risk. Further, the corrosion prediction system 150 can preemptively warn a user of that corrosion risk, such as by transmitting one or more notifications to the user.

In some implementations, the neural network 152 can receive data regarding a gas flow line 160, and output a metric based on the data. In some implementations, the metric can indicate the likelihood that the gas flow line 160 is currently corroded and/or the predicted severity of that corrosion. In some implementations, the metric can indicate the likelihood that the gas flow line 160 will develop corrosion in the future (for example, within a particular length of time in the future) and/or the predicted severity of that corrosion.

As an example, a metric having a high value can indicate that a gas flow line 160 is likely to be corroded and/or that the corrosion is predicted to be severe. Further, a metric having a low value can indicate that a gas flow line 160 is unlikely to be corroded and/or that the corrosion is predicted to be slight.

As another example, a metric having a high value can indicate that a gas flow line 160 is likely to become corroded on the future (for example, with a particular length of time in the future) and/or that the corrosion is predicted to be severe. Further, a metric having a low value can indicate that a gas flow line 160 is unlikely to become corroded in the future and/or that the corrosion is predicted to be slight.

In some implementations, the severity of corrosion can refer to the proportion of the gas flow line 160 that has been corroded (for example, relative to the total area, volume, or mass of the gas flow line 160). In some implementations, the severity of corrosion can refer to the presence, size, and/or number or holes, gaps, cracks, or other openings that have developed on the gas flow line due to corrosion. In some implementations, the severity of corrosion can refer to the degree in which the structural integrity of the gas flow line has been compromised due to corrosion. In some implementations, the severity of corrosion can refer to the likelihood that a gas leak has occurred and/or will occur along the gas flow line. In some implementations, the severity of corrosion can refer to the reduction in the maximum pressure of gas that the gas flow line can convey without failing (for example, without rupturing). In some implementations, the severity of corrosion can refer to the susceptibility of the gas flow line to corrosion in the future.

In some implementations, the corrosion prediction system 150 can preemptively warn a user regarding the likelihood that one or more of the gas flow lines 160 will become corroded in the future, prior to the corrosion developing and/or becoming severe enough to weaken the structural integrity of those gas flow lines 160. For instance, if the metric for a gas flow line 160 exceeds a particular threshold value (for example, indicating that the likelihood that gas flow line is corroded or will become corroded is sufficiently high), the corrosion prediction system 150 can generate a notification to a user to warn the user of the risk. Further, the corrosion prediction system 150 can identify specific gas flow line 160 that is at risk. This technique can be beneficial, for example, in assisting the user in identifying corrosion risks in the gas flow lines 160, and repairing and/or maintaining the gas flow lines 160 to avoid or otherwise mitigate the effects of corrosion.

Each of the computer systems 104a-104c can include any number of electronic device that are configured to receive, process, and transmit data. Examples of the computer systems 104a-104c include client computing devices (such as desktop computers or notebook computers), server computing devices (such as server computers or cloud computing systems), mobile computing devices (such as cellular phones, smartphones, tablets, personal data assistants, notebook computers with networking capability), wearable computing devices (such as a smart phone or a headset), and other computing devices capable of receiving, processing, and transmitting data. In some implementations, the computer systems 104a-104c can include computing devices that operate using one or more operating systems (as examples, Microsoft Windows, Apple macOS, Linux, Unix, Google Android, and Apple iOS, among others) and one or more architectures (as examples, x86, PowerPC, and ARM, among others). In some implementations, one or more of the computer system 104a-104c need not be located locally with respect to the rest of the system 100, and one or more of the computer systems 104a-104c can be located in one or more remote physical locations.

Each the computer systems 104a-104c can include a respective user interface that enables users interact with the computer system 104a-104c and the corrosion prediction system 150, such as to view data from one or more of the computer systems 104a-104c or the corrosion prediction system 150, transmit data from one computer system 104a-104c to another, or to issue commands to one or more of the computer systems 104a-104c or the corrosion prediction system 150. Commands can include, for example, any user instruction to one or more of the computer system 104a-104c or the corrosion prediction system 150 to perform particular operations or tasks. In some implementations, a user can install a software application onto one or more of the computer systems 104a-104c to facilitate performance of these tasks (for example, an installable front end application, described in further detail below).

In FIG. 1, the computer systems 104a-104c are illustrated as respective single components. However, in practice, the computer systems 104a-104c can be implemented on one or more computing devices (for example, each computing device including at least one processor such as a microprocessor or microcontroller). As an example, the computer system 104c can be a single computing device that is connected to the network 108, and the corrosion prediction system 150 can be maintained and operated on the single computing device. As another example, the computer system 104c can include multiple computing devices that are connected to the network 108, and the corrosion prediction system 150 can be maintained and operated on some or all of the computing devices. For instance, the computer system 104c can include several computing devices, and the corrosion prediction system 150 can be distributed on one or more of these computing devices.

The network 108 can be any communications network through which data can be transferred and shared. For example, the network 108 can be a local area network (LAN) or a wide-area network (WAN), such as the Internet. The network 108 can be implemented using various networking interfaces, for instance wireless networking interfaces (such as Wi-Fi, Bluetooth, or infrared) or wired networking interfaces (such as Ethernet or serial connection). The network 108 also can include combinations of more than one network, and can be implemented using one or more networking interfaces.

In general, the corrosion prediction system 150 can predict a corrosion risk in the gas flow lines 160 based on sensor data 112, operations data 114, and training data 116.

The sensor data 112 represents one or more properties of the gas flow lines 160 and/or the gaseous substances therein. The sensor data 112 can be generated, at least in part, by one or more sensors 106 positioned in or around the gas flow lines 160. In some implementations, the sensor data 112 can be generated by the sensors 106 and provided to the corrosion prediction system 150 in real time or substantially real time.

In some implementations, at least one of the sensors 106 can be a flow rate sensor that is configured to generate sensor data representing a flow rate of gas through one or more of the gas flow lines 160.

In some implementations, at least one of the sensors 106 can be a pressure sensor that is configured to generate sensor data representing a pressure of gas within one or more of the gas flow lines 160.

In some implementations, at least one of the sensors 106 can be a composition sensor that is configured to generate sensor data representing the composition of gas within one or more of the gas flow lines 160. As an example, a gas composition sensor can identify one or hydrocarbon gases within a gas flow line 160. As another example, a gas composition sensor can identify one or more additives within a gas flow line 160, such as substances that are introduced into the gas flow line 160 to inhibit corrosion. Example additives include water-soluble organic corrosion inhibitors.

In some implementations, at least one of the sensors 106 can be a temperature sensor that is configured to generate sensor data representing a temperature of gas within one or more of the gas flow lines 160.

In some implementations, at least one of the sensors 106 can be a temperature sensor that is configured to generate sensor data representing a temperature of an exterior environment of one or more of the gas flow lines 160.

The operations data 114 represents one or more aspects of the operation of the gas flow lines 160. The operations data 114 can be generated, at least in part, by a computer system 104b that controls and/or monitors the operation of the gas flow lines 160. In some implementations, the operations data 114 can include data regarding a present state of the gas flow lines 160. In some implementations, the operations data 114 can include data regarding an anticipated future state of the gas flow line 160 (for example, data regarding a planned future operation of the gas flow lines 160). In some implementations, the operations data 114 can include data regarding a previous state of the gas flow line 160 (for example, data regarding a previously performed operation of the gas flow lines 160).

In some implementations, the operations data 114 can include data regarding the composition of gaseous substances that are (or are anticipated to be) conveyed through the gas flow lines 160. As an example, the operations data 114 can indicate one or more hydrocarbons in or anticipated to be in the gaseous substances. As another example, the operations data 114 can indicate one or more additives in or anticipated to be in the gaseous substances.

In some implementations, the operations data 114 can include data regarding the flow rate of gaseous substances that are (or are anticipated to be) conveyed through the gas flow lines 160.

In some implementations, the operations data 114 can include data regarding the pressure of gaseous substances that are (or are anticipated to be) conveyed through the gas flow lines 160.

In some implementations, the operations data 114 can include data regarding the length of time in which gaseous substances are (or are anticipated to be) conveyed through the gas flow lines 160. For example, the operations data 114 can indicate the length of time that each of the gas flow lines 160 has been in use or will be in use.

In some implementations, the operations data 114 can include data regarding the physical configuration of the gas flow lines 160. As an example, the operation data 114 can indicate the physical dimensions of each of the gas flow lines (for example, length, width, inner diameter, outer diameter, trajectory, or any other physical dimension of the gas flow line). As another example, the operation data 114 can indicate the composition of each of the gas flow lines (for example, the materials or materials that were used to construct the gas flow line). As another example, the operation data 114 can indicate the structure of each of the gas flow lines (for example, the shape the components that form the gas flow line, and the arrangement of those components relative to one another).

As described above, the corrosion prediction system 150 can use training data 116 to train the neural network 152 to recognize characteristics of the gas flow lines 160 that are indicative to a corrosion risk. As an example, the corrosion prediction system 150 can obtain multiple sets of training data 116, each set including (i) properties of a respective previously observed gas flow line, and (ii) an indication of the extent of corrosion in that gas flow line (for example, whether that gas flow line has corroded or later become corroded, and if so, the severity of that corrosion). Further, the corrosion prediction system 150 can train the neural network 152 to recognize particular trends, patterns, or correlations between the characteristics of the properties of the previously observed gas flow lines, and the extent of corrosion of those gas flow lines. Example training data and training techniques are described in further detail below.

The data in each set of training data 116 can be similar to the sensor data 112 and/or the operations data 114 described above. For instance, each set of training data 116 can include sensor data regarding a respective previously observed gas flow line, such as a flow rate of gas through that gas flow line, a pressure of gas in that gas flow line, the composition of gas within that gas flow line, a temperature of gas within that gas flow line, or any other sensor data. Further, each set of training data 116 can include operations data regarding a respective previously observed gas flow line, such as data regarding the physical configuration of the gas flow line, the characteristics of the gaseous substances that were conveyed in that gas flow line, the properties of the exterior environment of that gas flow line, or any other operations data.

Further, each set of training data can include an extent of corrosion in a respective previously observed gas flow line. For example, the training data can indicate whether the gas flow line was corroded at the time that the sensor data and/or operations data was obtained, and if so, the severity of that corrosion. As another example, the training data can indicate whether the gas flow line become corroded after the sensor data and/or operations data was obtained, and if so, the severity of that corrosion, the time at which the corrosion developed, and/or the progression of that corrosion over time. In some implementations, at least some of the data regarding the corrosion (or lack thereof) in a gas flow line can be based on a user's inspections of a respective gas flow line, sensor data, or any other information.

Figure 2:
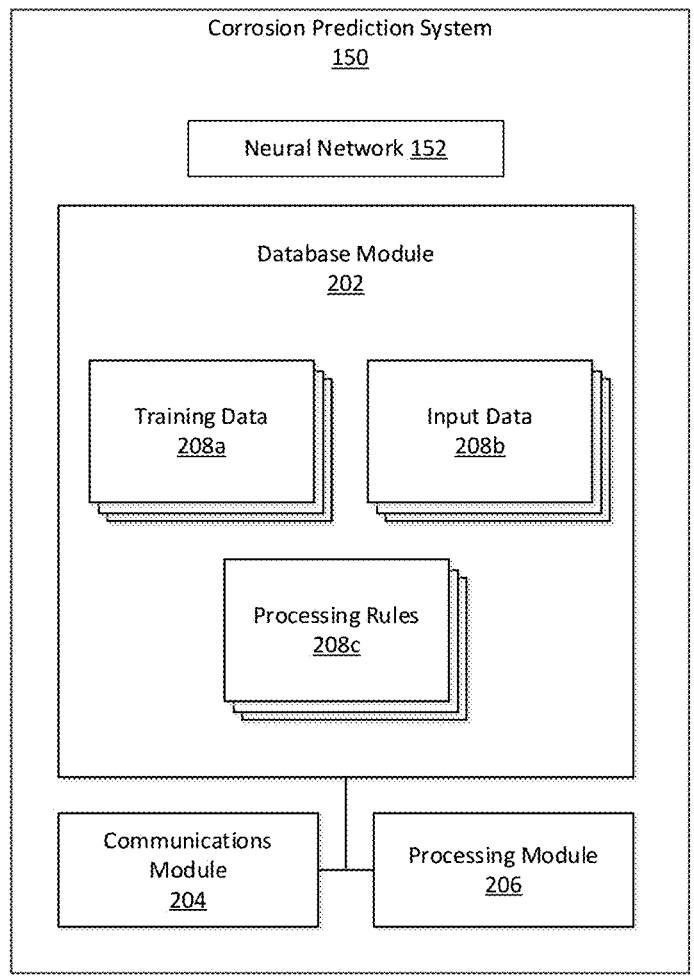
FIG. 2 is a diagram of an example corrosion prediction system.

FIG. 2 shows various aspects of the corrosion prediction system 150. The corrosion prediction system 150 includes a neural network 152 and several modules that perform particular functions related to the operation of the system 100. For example, the corrosion prediction system 150 can include a database module 202, a communications module 204, and a processing module 206.

The database module 202 maintains information related to predicting corrosion in the gas flow lines 160 using the neural network 152. As an example, the database module 202 can store training data 208a that is used to train the neural network 152 to predict corrosion in the gas flow lines 160. The training data 208a can include historical information regarding one or more previously observed gas flow lines and information regarding whether corrosion developed in those gas flow lines. In some implementations, the training data 208a can be similar to the training data 116 described with respect to FIG. 1.

Further, the database module 202 can store input data 208b to be used to predict corrosion in one or more presently observed gas flow lines. As an example, the input data 208b can include the sensor data 112 and/or the operations data 114 described with respect to FIG. 1.

Further, the database module 202 can store processing rules 208c specifying how data in the database module 202 can be processed to train a neural network 152 to predict corrosion in the gas flow lines 160. For instance, the processing rules 208c can specify how the training data 208a is used by the corrosion prediction system 150 to train a neural network 152 to predict corrosion in the gas flow lines 160 based on the input data 208b.

For example, the processing rules 208c can specify one more machine learning or artificial intelligence processes for identifying patterns, trends, or correlations in the input data that indicate that corrosion has developed or is likely to develop in the future. As another example, the processing rules 208c can specify that at least a portion of the training data 208a be used as input data in the machine learning or artificial intelligence processes (for example, to provide "ground truth" examples that can aid in the identification of patterns or trends). Accordingly, the corrosion prediction system 150 can be trained to predict corrosion in newly observed gas flow lines based on information regarding previously observed gas flow lines. In some implementations, the processing rules 208c can specify that the neural network 152 be iteratively trained and re-trained with successive sets of training data 208a (for example, additional sets of training data 208a that are collected over time) to progressively improve its accuracy in predicting corrosion in gas flow lines. In some implementations, the processing rules 208c can specify that a training process be performed automatically by the corrosion prediction system 150 without manual user input.

As another example, the processing rules 208c can specify that the neural network 152 receives the input data 208b, and outputs a metric based on the input data 208b. As described above, the metric can indicate the likelihood that the gas flow line corresponding to the input data 208b is corroded, the likelihood that the gas flow line corresponding to the input data 208*b* will become corroded, and/or the predicted severity of that corrosion.

Example machine learning or artificial intelligence process are described in further detail below.

In some implementations, the processing rules 208*c* can specify that the corrosion prediction system 150 preemptively warns a user regarding the likelihood that corrosion will develop in a particular gas flow line 160, prior to the corrosion developing and/or becoming severe enough to weaken the structural integrity of those gas flow lines 160. For instance, the processing rules 208*c* can specify that if the metric exceeds a first threshold value (for example, indicating that the likelihood that gas flow line is corroded or will become corroded is sufficiently high), in response, the corrosion prediction system 150 will generate a notification to a user to warn the user of the risk. Further, the corrosion prediction system 150 can identify specific gas flow line 160 that is at risk.

As described above, the corrosion prediction system 150 also includes a communications module 204. The communications module 204 allows for the transmission of data to and from the corrosion prediction system 150. For example, the communications module 204 can be communicatively connected to the network 108, such that it can transmit data to and receive data from each of the computer systems 104*a*-104*c* and the sensors 106. Information received from the computer systems 104*a*-104*c* and sensors 106 can be processed (for example, using the processing module 206) and stored (for example, using the database module 202).

Further, the communications module 204 can generate a notification to one or more users regarding the predicted corrosion risk in one or more of the gas flow lines 160. As an example, the communications module can generate one or more e-mails, chat messages, text messages (for example, Short Message Service messages), voice messages, video messages, audio messages, and/or any other notification, and transmit that notification to a communications device of a user (for example, via the communications network 108). Example communications devices include network-enabled client computing devices, server computing devices, mobile computing devices, wearable computing devices, telephones, pagers, beepers, or any other computing device capable of receiving and/or transmitting data.

In some implementations, the notification can indicate a predicted risk of one or more of the gas flow lines 160. Further, the notification can identify one or more particular gas flow lines 160 that have corroded or at risk of corroding. Further, the notification can identify the predicted severity of that corrosion.

As described above, the corrosion prediction system 150 also includes a processing module 206. The processing module 206 processes data stored or otherwise accessible to the corrosion prediction system 150. For instance, the processing module 206 can generate the neural network 152 to predict corrosion in the gas flow lines 160, given particular training data 208*a* and processing rules 208*c*. Further, the processing module 206 can determine a likelihood that a particular gas flow line 160 is corroded (or will become corroded), based on the neural network 152 and given particular input data 208*b*.

Further, the processing module 206 can modify the neural network 152 based the training data 208*a* and the processing rules 208*c*. For example, as described above, the processing module 206 can perform one or more machine learning or artificial intelligence processes to identify patterns, trends, or correlations in input data that indicate a corrosion risk of a gas flow line 160. The identified patterns, trends, or correlations can be used to generate or modify one or more of the processing rules 208*c* for generating and updating the neural network 152 (for example, to distinguish between different sets of input data and predicted risks). Further, as described above, at least a portion of the training data 208*a* can be used as input data in the machine learning or artificial intelligence processes. Further, as described above, the processing module 206 can perform the training processes iteratively using successive sets of training data 208*a* to progressively improve the neural network's accuracy in predicting corrosion risks in the gas flow lines 160. In some implementations, this training process can be performed automatically by the processing module 206 without manual user input.

In some implementations, a software application can be used to facilitate performance of the tasks described herein. As an example, a front-end application can be installed one or more of the computer systems 104*a*-104*c*. Further, a user can interact with the front-end application to input data and/or commands to the corrosion prediction system 150, and review data generated by the corrosion prediction system 150.

In some implementations, the front-end application can present a dashboard user interface (for example, a graphical user interface) that includes information regarding one or more of the gas flow lines 160. As an example, the user interface can identify each of the gas flow lines 160 that are being monitored by the corrosion prediction system 150. As another example, for each of the gas flow lines 160, the user interface can indicate a risk of corrosion for that gas flow line 160, a predicted severity of corrosion for that flow line 160, the operating conditions of that gas flow line 160, and/or any other information regarding that gas flow line 160.

In some implementations, the user interface can present information regarding several gas flow lines 160 concurrently. Further, the user interface can enable a user to select one or more of the gas flow lines 160, and retrieve more detailed information regarding the selected gas flow lines 160. This can be beneficial, for example, as it enables the user to oversee several gas flow lines concurrently, while also enabling the user to evaluate a particular gas flow line in greater detail as desired. For instance, the user interface can present a "summary view" showing the statuses of several gas flow lines 160 concurrently. Further, a user can select a particular gas flow line to view detailed information regarding the selected flow line, such as the risk of corrosion for that gas flow line 160, a predicted severity of corrosion for that flow line 160, the operating conditions of that gas flow line 160, and/or any other information regarding that gas flow line 160.

Figure 3A:
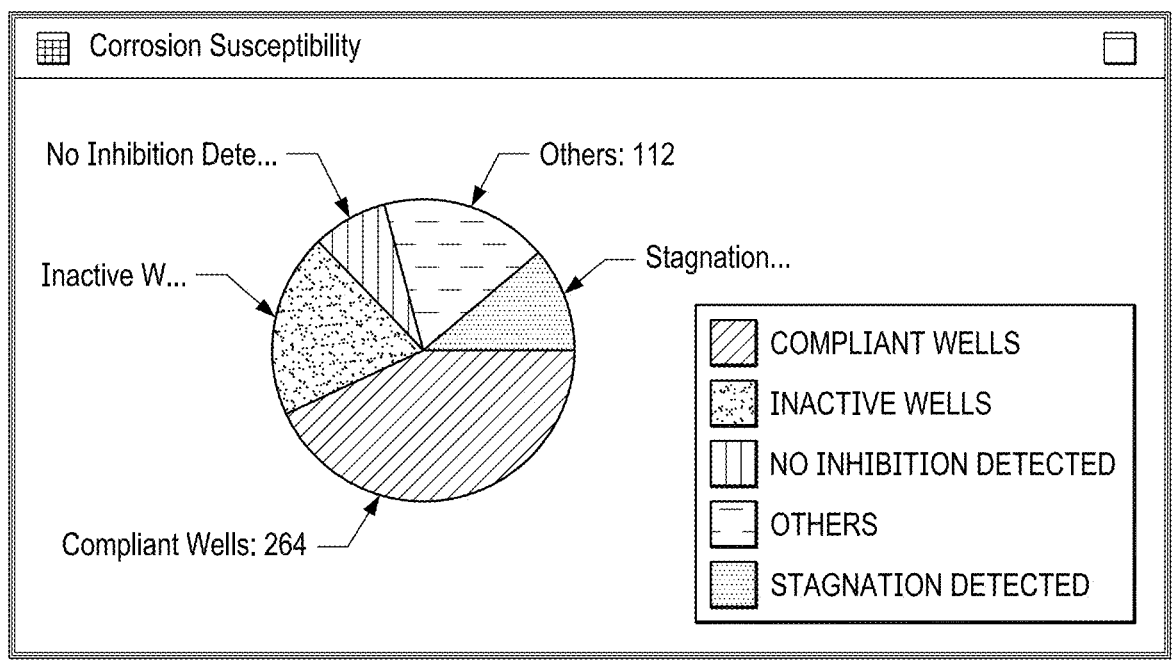
FIGS. 3A and 3B are diagrams of example graphical user interfaces of a front-end application.
Figure 3B:
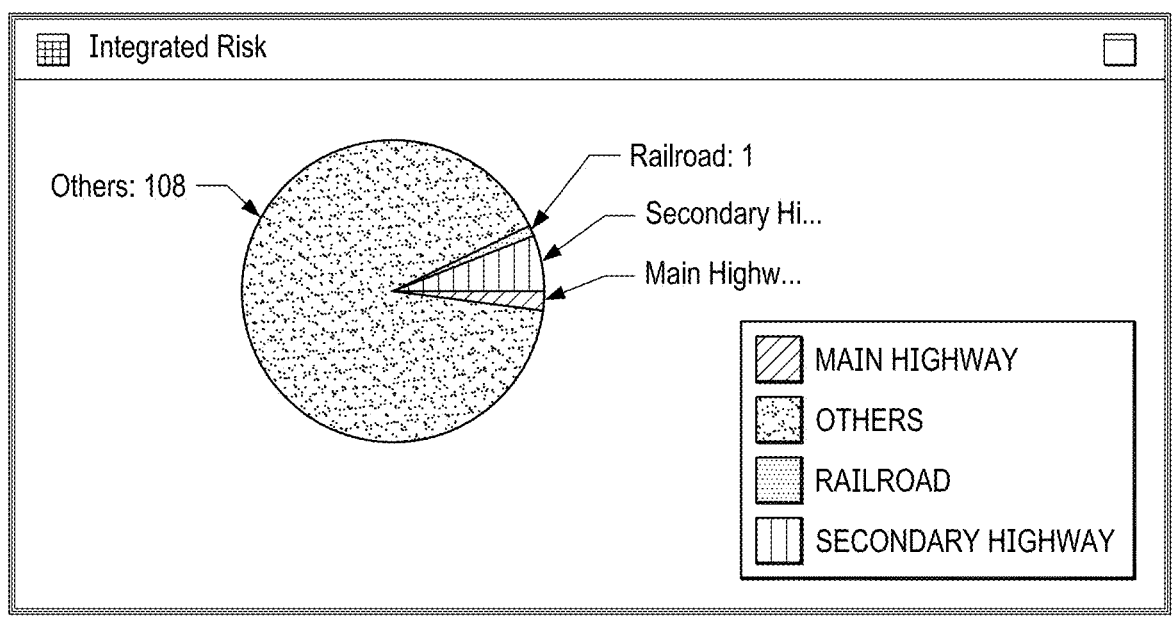

Example graphical user interfaces 300 and 310 are shown in FIGS. 3A and 3B, respectively. As shown in FIGS. 3A and 3B, a graphical user interface can present information regarding multiple gas flow lines concurrently in the form of a pie graph. Gas flow lines can be grouped into different categories based on their characteristics, such as each gas flow line's operational status, level of corrosion risk, predicted severity of corrosion, and/or location. A user can select a particular group to retrieve further information regarding the gas flow lines in that group.

As described above, the corrosion prediction system 150 can generate a notification to one or more users regarding the predicted corrosion risk in one or more of the gas flow lines 160. In some implementations, the front-end application can be used to generate and present at least some notifications to a user. For example, the front-end application can be configured to present graphical, auditory, and/or textual content to indicate any of the information described herein. For instance, the front-end application can indicate a predicted risk of one or more of the gas flow lines 160. Further, the front-end application can identify one or more particular gas flow lines 160 that have corroded or are at risk of corroding. Further, the front-end application can identify the predicted severity of that corrosion.

In some implementations, the front-end application can enable a user to customize the manner in which notifications are generated and presented. As an example, the front-end application can enable a user to specify one or more recipients for notifications, and the types of notifications that are used to contact each of those recipients (for example, e-mails, chat messages, text messages, voice messages, video messages, audio messages, or any other type of notification).

In some implementations, the front-end application can enable a user to assign different recipients to different respective gas flow lines 160. For example, the front-end application can enable a user to assign a first set of recipients to a first gas flow line, a second set of recipients to a second gas flow line, a third set of recipients to a third gas flow line, and so forth. This can be beneficial, for example, as it enables the corrosion prediction system 150 to provide notifications to users in a targeted manner. For instance, if a corrosion risk is detected for a particular gas flow line, the corrosion prediction system 150 can selectively notify the users who are responsible for maintaining that gas flow line, rather than notifying each and every user of the corrosion prediction system 150.

In some implementations, the front-end application can enable a user to export information from the corrosion prediction system 150, including any of the information described above. For example, the front-end application can be used to export some or all of the sensor data 112, the operations data 114, the training data 116, and/or the metrics or predictions generated by corrosion prediction system 150. The front-end application can export information according to any format or file type. As an example, the front-end application can export at least some of the information in the form of a spreadsheet, such as a Microsoft Excel file.

Figure 4:
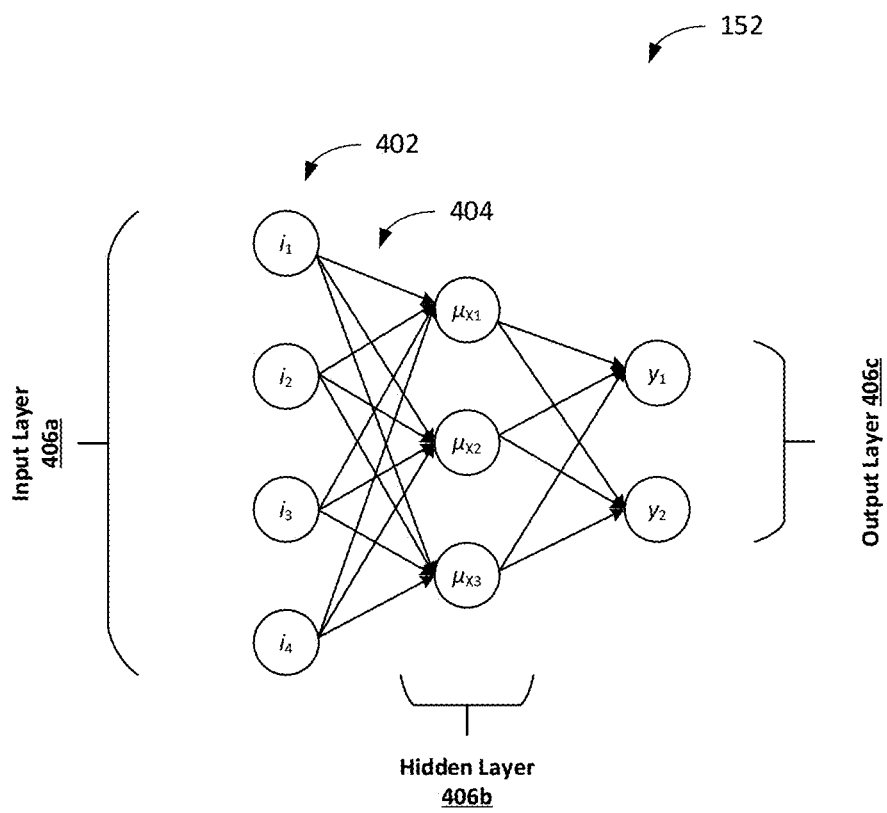
FIG. 4 is a diagram of an example neural network.

As described above, a machine learning or particular intelligence process can be performed using one or more neural networks 152. A simplified example of a neural network 152 is shown in FIG. 4.

The neural network 152 includes several nodes 402 (often called "neurons") interconnected with another by interconnections 404. Further, the nodes 402 are arranged according to multiple layers, including an input layer 406a, a hidden layer 406b, and an output layer 406c. The arrangement of the nodes 402 and the interconnections 404 between them represent a mathematical transformation of input data (for example, as received by the nodes of the input layer 406a) into corresponding output data (for example, as output by the nodes of the output layer 406c). In some implementations, the input data can represent one or more data points obtained by the corrosion prediction system 150, and the output data can represent one or more corresponding metrics or predictions generated by the corrosion prediction system 150 based on the input data.

The nodes 402 of the input layer 406a receive input values and output the received input values to respective nodes of the next layer of the neural network 152. In this example, the neural network 152 includes several inputs $i_1$, $i_2$, $i_3$, and $i_4$, each of which receives a respective input value and outputs the received value to one or more of the nodes $\mu_{x1}$, $\mu_{x2}$, and $\mu_{x3}$ (for example, as indicated by the interconnections 404).

In some implementations, at least some of the information stored by the database module (for example, the input data 208b) can be used as inputs for the nodes of the input layer 406a. For example, at least some of the information stored by the database module can be expressed numerically (for example, assigned a numerical score or value), and input into the nodes of the input layer 406a.

The nodes of the hidden layer 406b receive input values (for example, from the nodes of the input layer 406a or nodes of other hidden layers), applies particular transformations to the received values, and outputs the transformed values to respective nodes of the next layer of the neural network 152 (for example, as indicated by the interconnections 404). In this example, the neural network 152 includes several nodes $\mu_{x1}$, $\mu_{x2}$, and $\mu_{3}$, each of which receives respective input values from the nodes $i_1$, $i_2$, $i_3$, and $i_4$, applies a respective transformation to the received values, and outputs the transformed values to one or more of the nodes $y_1$ and $y_2$.

In some implementations, nodes of the hidden layer 406b can receive one or more input values, and transform the one or more received values according to a mathematical transfer function. As an example, the values that are received by a node can be used as input values in particular transfer function, and the value that is output by the transfer function can be used as the output of the node. In some implementations, a transfer function can be a non-linear function. In some implementations, a transfer function can be a linear function.

In some implementations, a transfer function can weight certain inputs differently than others, such that certain inputs have a greater influence on the output of the node than others. For example, in some implementations, a transfer function can weight each of the inputs by multiplying each of the inputs by a respective coefficient. Further, in some implementations, a transfer function can apply a bias to its output. For example, in some implementations, a transfer function can bias its output by a particular offset value.

For instance, a transfer function of a particular node can be represented as:

$$Y = \sum_{i=1}^{n}(\text{weight}_i * \text{input}_i) + \text{bias},$$

where $\text{weight}_i$ is the weight that is applied to an input $\text{input}_i$, bias is a bias or offset value is that is applied to the sum of the weighted inputs, and Y is the output of the node.

The nodes of the output layer 406c receive input values (for example from the nodes of the hidden layer 406b) and output the received values. In some implementations, nodes of the output layer 406c can also receive one or more input values, and transform the one or more received values according to a mathematical transfer function (for example, in a similar manner as the nodes of the hidden layer 406b). As an example, the values that are received by a node can be used as input values in particular transfer function, and the value that is output by the transfer function can be used as the output of the node. In some implementations, a transfer function can be a non-linear function. In some implementations, a transfer function can be a linear function.

In some implementations, at least one of the nodes of the output layer 406c can correspond to a metric that indicates the likelihood that one or more gas flow lines 160 are corroded (or will become corroded) given particular input data regarding those gas flow lines. As an example a metric having a high value can indicate that a particular gas flow line 160 is likely to be corroded (or likely to become corroded), whereas a metric having a low value can indicate that the input data is not likely to be corroded (or not likely to become corroded).

In this example, the neural network 152 includes two output nodes $y_1$ and $y_2$, each of which receives respective input values from the nodes $\mu_{x1}$, $\mu_{x2}$, and $\mu_{x3}$, applies a respective transformation to the received values, and outputs the transformed values as outputs of the neural network 152.

Although FIG. 4 shows example nodes and example interconnections between them, this is merely an illustrative example. In practice, a neural network can include any number of nodes that are interconnected according to any arrangement. Further, although FIG. 4 shows a neural network 152 having a single hidden layer 406b, in practice, a network can include any number of hidden layers (for example, one, two, three, four, or more), or none at all.

Figure 5:
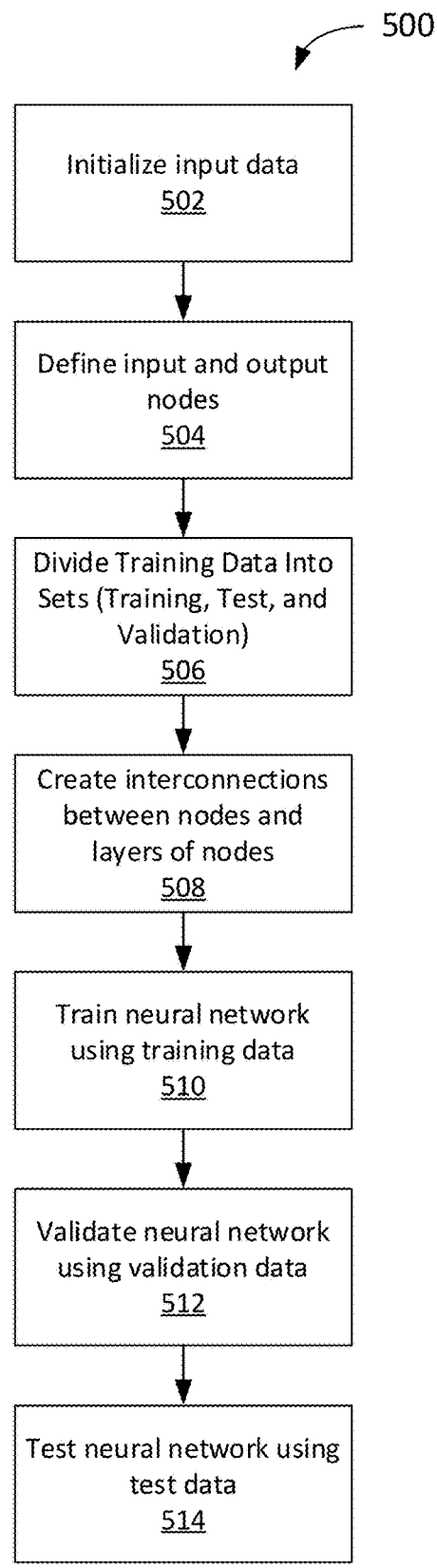
FIG. 5 is a flow chart diagram of an example process for training a neural network.

In some implementations, the neural network 152 can be trained based on training data, such as the training data 208a stored in the database module 202. An example process 500 for training the neural network 152 is shown in FIG. 5.

According to the process 500, the corrosion prediction system 150 initializes the input data that is used to train the neural network 152 (block 502). As an example, the corrosion prediction system 150 can retrieve at least a portion of the training data 208a, as described above.

Further, the corrosion prediction system 150 defines the input and the output nodes of the neural network 152 (block 504). For example, the corrosion prediction system 150 can select one or more of the types of data include in the training data 208a (for example, as described above), and specify that they be used as respective input nodes in the neural network 152 (for example, as inputs for respective nodes of the input layer 406a). As another example, the corrosion prediction system 150 can specify each of the outputs of the neural network (for example, the outputs of each of the nodes of the output layer 406c). For instance, at least one of the nodes of the output layer 406c can correspond to the likelihood that a particular gas flow line 160 is corroded (or will become corroded). Further, in some implementations, at least one of the nodes of the output layer 406c can correspond to the severity of that corrosion.

The corrosion prediction system 150 divides the training data 208a into different sets (block 506). For example, the training data 208a can be divided into a training set, a validation set, and a test set.

The training set can be used to train the neural network 152. For example, the training set can be used to identify patterns, trends, or correlations between the inputs and the outputs of the neural network 152, and to express those relationships using the nodes and interconnections between them.

The validation set can be used to tune the performance of the trained neural network 152. For example, the validation set can be used to determine a difference between the output of the neural network 152 given certain inputs, and an expected output. The configuration of the neural network can be modified based on the different (for example, such that the output of the neural network 152 better matches the expected result).

The test set can be used to evaluate the performance of the trained neural network 152 (for instance, after it has been tuned based on the validation set). For example, the test set can be used to determine a difference between the output of the neural network 152 given certain inputs, and an expected output. This difference can indicate the ability of the neural network 152 to accurately predict a particular outcome (for example, likelihood that a gas flow line has corroded or will become corroded) given particular inputs (for example, particular sensor data and/or operations data).

Further, the corrosion prediction system 150 creates interconnections between the nodes and layers of nodes in of the neural network 152 (block 508). In some implementations, an interconnection between two or more nodes can be in the forward direction (for example, data can be passed between nodes in the direction of the input to the output of the neural network 152). This may be referred to as a "feed forward" interconnection. In some implementations, an interconnection between two or more nodes can be in the backward direction (for example, data can be passed between nodes in the direction of the output to the input of the neural network 152). This may be referred to as a "back propagation" interconnection.

Further, the corrosion prediction system 150 creates layers of nodes. For example, the corrosion prediction system 150 can specify that the neural network include N layers of nodes, such as one input layer, one output layer, and N−2 hidden layers. Other arrangements of layers are also possible, depending on the implementation.

Further, the corrosion prediction system 150 trains the neural network 152 using the training set (block 510). In some implementations, the corrosion prediction system 150 can perform the training based on a supervised learning method. As an example, the training set can include example input data and output data. Based on the arrangement of the nodes and the interconnections between them, the corrosion prediction system 150 can identify transfer functions for each of the nodes that would result in the output of the neural network 152 matching or otherwise being similar to the output data in the training set, given the same input data. In some implementations, the corrosion prediction system 150 can select particular weights or biases for each of the transfer functions. In some implementations, this can be performed iteratively (for example, using successive sets of training data).

After training the neural network 152, the corrosion prediction system 150 validates the neural network 152 using the validation set (block 512). As an example, the validation set can include example input data and output data. The corrosion prediction system 150 can input the input data into the neural network 152, and compare the output of the neural network 152 to the output data of the validation set. In some implementations, the corrosion prediction system 150 can calculate an "error" of the neural network 152, such as the difference between the output data of the validation set and the output of the neural network 152.

In some implementations, the corrosion prediction system 150 can tune the neural network 152 based on the validation set. For example, the corrosion prediction system 150 can modify the arrangement of the nodes, the interconnections between them, and/or the transfer functions (for example, the weights and biases) such that the error of the neural network 152 is reduced.

In some implementations, this can be performed iteratively (for example, using successive sets of validation data) until particular criteria are met. For example, in some implementations, the corrosion prediction system 150 can iteratively tune the neural network 152 until the error of the neural network 152 is less than a particular threshold value. As another example, the corrosion prediction system 150 can iteratively tune the neural network 152 until the neural network 152 exhibits a sufficiently low false positive rate (for example, the rate in which it predicts that corrosion has developed and/or will develop, when in fact corrosion has not developed and/or will not develop) and/or a sufficiently low false negative rate (for example, the rate in which it predicts that corrosion has not developed and/or will not develop, when in fact corrosion has developed and/or will develop).

After training and tuning the neural network 152, the corrosion prediction system 150 tests the neural network 152 using the test set (block 514). As an example, the test set can include example input data and output data. The corrosion prediction system 150 can input the input data into the neural network 152, and compare the output of the neural network 152 to the output data of the test set. In some implementations, the corrosion prediction system 150 can calculate an "error" of the neural network 152, such as the difference between the output data of the test set and the output of the neural network 152. This error can represent the predictive performance of the neural network 152. For example, a high error can indicate that the neural network 152 is not likely to predict an outcome accurately, given certain input data. Conversely, lower error can indicate that the neural network 152 is likely to predict an outcome accurately, given certain input data.

In some implementations, the metric can be categorized into different discrete levels of severity. For example, if the metric for a particular for a particular gas flow line 160 is less than a first threshold value, the metric for that gas flow line 160 can be categorized as a "low" severity level (for example, indicating a low risk of corrosion). As another example, if the metric for a gas flow line is greater than or equal to the first threshold value and less than a second threshold value, the metric for that gas flow line can be categorized as a "medium" severity level (for example, indicating a moderate risk of corrosion). As another example, if the metric for a gas flow line is greater than or equal to the second threshold value and less than a third threshold value, the metric for that gas flow line can be categorized as a "high" severity level (for example, indicating a high risk of corrosion).

As another example, if the matric for a gas flow line is less than a particular threshold value, the metric for the gas flow line can be categorized a "no risk" (for example, indicating that there is substantially no risk of corrosion).

Although example categories are described above, these are merely illustrative examples. In practice, a metric can be categorized according to any number and/or distribution of severity levels.

In some implementations, the corrosion prediction system 150 can inspect the training data 208a and/or the input data 208b, and modify the training data 208a and/or the input data 208b to improve the performance of the corrosion prediction system 150. This process may be referred to as "cleansing" and/or "transforming" the data.

For instance, the corrosion prediction system 150 can inspect the training data 208a and/or the input data 208b, and determine whether the training data 208a and/or the input data 208b is incomplete. As an example, input data 208b may be incomplete if at least some sensor data and/or operations data is absent for particular time points (for example, indicating that measurements were not obtained at certain time points, or that those measurements were lost of corrupted). As an example, input data 208b may be incomplete if at least some sensor data and/or operations data is absent for particular gas flow lines. In response, the corrosion prediction system 150 can modify the input data 208b to avoid or otherwise mitigate the effects of the incomplete data. For instance, the corrosion prediction system 150 can obtain at least some of the missing data, and insert the missing data into the input data 208b. The missing data can be obtained for example, from a database storing sensor data and/or operations data from the presently observed gas flow lines.

Further, training data 208a may be incomplete if at least some sensor data, operations data, and/or corrosion data is absent for particular time points (for example, indicating that measurements were not obtained at certain time points, or that those measurements were lost or corrupted). As an example, training data 208a may be incomplete if at least some sensor data, operations data, and/or corrosion data is absent for particular gas flow lines. In response, the corrosion prediction system 150 can modify the training data 208a to avoid or otherwise mitigate the effects of the incomplete data. For instance, the corrosion prediction system 150 can obtain at least some of the missing data, and insert the missing data into the training data 208a. The missing data can be obtained for example, from a database storing sensor data and/or operations data from the previously observed gas flow lines.

Further, the corrosion prediction system 150 can inspect the training data 208a and/or the input data 208b, and determine whether the training data 208a and/or the input data 208b is inaccurate. As an example, input data 208b and/or training data 208a may be inaccurate if at least some sensor data and/or operations data is not consistent with the condition or state of the corresponding gas flow line. Inaccuracies in the data may be result of an erroneous operation of the sensors 106, a mis-calibration or misconfiguration of the sensors 106, a data entry error, corruption in the storage or transfer of the data, or any other circumstance that may adversely affect the accuracy of the data. In response, the corrosion prediction system 150 can modify the input data 208b and/or the training data 208a to correct the inaccurate data and/or mitigate the effects of the inaccurate data. For instance, the corrosion prediction system 150 can obtain additional sensor data and/or additional operational data from one or more additional sources (for example, other sensors or databases), and replace at least some of the inaccurate data with the additional sensor data and/or additional operational data.

Further, although example neural networks are provided, other types of machine learning system can be used to implement some or all of the techniques described herein, either instead of our in addition to neural networks. Example machine learning systems include decision tree systems, support-vector machines, regression analysis systems, Bayesian networks, and genetic algorithms, among others.

Example Processes

Figure 6:
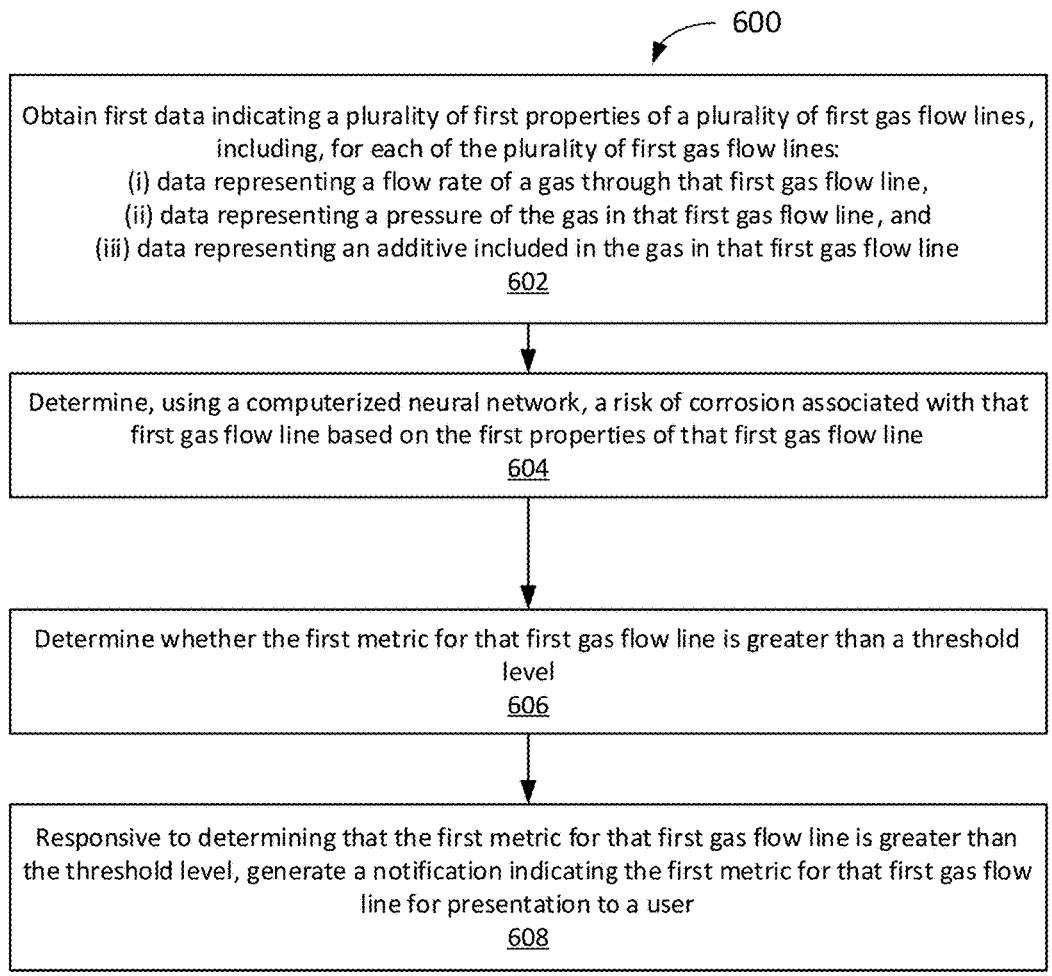
FIG. 6 is a flow chart diagrams of example processes for predicting corrosion in gas flow lines using machine learning.

FIG. 6 shows an example process 600 for predicting corrosion in gas flow lines using machine learning. In some implementations, the process 600 can be performed by the system 100 described in this disclosure (for example, the system 100 including the corrosion prediction system 150 shown and described with respect to FIGS. 1 and 2) using one or more processors (for example, using the processor or processors 710 shown in FIG. 7).

In the process 600, a system obtains first data indicating a plurality of first properties of a plurality of first gas flow lines (block 602). In some implementations, at least some of the gas flow lines can include one or more hydrocarbon gas flow lines.

The plurality of first properties includes, for each of the plurality of first gas flow lines: (i) data representing a flow rate of a gas through that first gas flow line, (ii) data representing a pressure of the gas in that first gas flow line, and (iii) data representing an additive included in the gas in that first gas flow line. Example additives include substances for inhibiting corrosion in one or more of the first gas flow lines.

In some implementations, the plurality of first properties can also include, for each of the plurality of first gas flow lines, a composition of the gas in that first gas flow line.

In some implementations, the plurality of first properties can also include, for each of the plurality of first gas flow lines, a composition of that first gas flow line.

In some implementations, the first data can include at least some of the sensor data 112, operations data 114, and/or input data 208*b* described with reference to FIGS. 1 and 2.

Further, the system performs additional operations for each of the plurality of first gas flow lines.

For example, the system determines, using a computerized neural network, a risk of corrosion associated with that first gas flow line based on the first properties of that first gas flow line (block 604). Example techniques for determining a risk of corrosion are described above, for example with reference to FIGS. 1-4.

Further, the system determines whether the first metric for that first gas flow line is greater than a threshold level (block 606).

Further, responsive to determining that the first metric for that first gas flow line is greater than the threshold level, the system generates a notification indicating the first metric for that first gas flow line for presentation to a user (block 608). As an example, the system can generate a notification such as an e-mail, a chat message, a text message, a voice message, a video message, an audio message, or any other notification. Further, the system can transmit that notification to a communications device of a user (for example, via the communications network 108).

In some implementations, the system can also determine, for each of the plurality of first gas flow lines, a degree of severity of the risk of corrosion associated with that first gas flow line.

In some implementations, the computerized neural network can be trained based a plurality of sets of training data. Each of the plurality of sets of training data can include second data indicating a plurality of second properties of a plurality of second gas flow lines.

Further, the plurality of second properties can include, for each of the plurality of second gas flow lines: (i) data representing a flow rate of a gas through that second gas flow line, (ii) data representing a pressure of the gas in that second gas flow line, (iii) data representing a second additive included in the gas in that second gas flow line (for example, a substance for inhibiting corrosion in that second gas flow line, and (iv) data representing an extent of corrosion in that second gas line.

In some implementations, the second data can include at least some of the training data 208*a* described with reference to FIG. 2.

In some implementations, the system can also determine that the first data includes incomplete data regarding one or more of the plurality of first gas flow lines, and in response, modify the first data to include additional data regarding the one or more of the plurality of first gas flow lines.

In some implementations, the system can also determine that the first data includes inaccurate data regarding one or more of the plurality of first gas flow lines, and in response, modify the first data to correct the inaccurate data regarding the one or more of the plurality of first gas flow lines.

Example Systems

Some implementations of the subject matter and operations described in this specification can be implemented in digital electronic circuitry, or in computer software, firmware, or hardware, including the structures disclosed in this specification and their structural equivalents, or in combinations of one or more of them. For example, in some implementations, one or more components of the system 100 and the corrosion prediction system 150 can be implemented using digital electronic circuitry, or in computer software, firmware, or hardware, or in combinations of one or more of them. In another example, the processes 500 and 600 shown in FIGS. 5 and 6 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, that is, one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer can also include, or be operatively coupled to receive data from or transfer data to, or both, one or more mass storage devices for storing data, for example, magnetic, magneto optical disks, or optical disks. However, a computer need not have such devices. Devices suitable for storing computer program instructions and data include all forms of non-volatile memory, media and memory devices, including by way of example semiconductor memory devices (for example, EPROM, EEPROM, AND flash memory devices), magnetic disks (for example, internal hard disks, and removable disks), magneto optical disks, and CD-ROM and DVD-ROM disks. The processor and the memory can be supplemented by, or incorporated in, special purpose logic circuitry.

To provide for interaction with a user, operations can be implemented on a computer having a display device (for example, a monitor, or another type of display device) for displaying information to the user. The computer can also include a keyboard and a pointing device (for example, a mouse, a trackball, a tablet, a touch sensitive screen, or another type of pointing device) by which the user can provide input to the computer. Other kinds of devices can be used to provide for interaction with a user as well. For example, feedback provided to the user can be any form of sensory feedback, such as visual feedback, auditory feedback, or tactile feedback. Input from the user can be received in any form, including acoustic, speech, or tactile input. In addition, a computer can interact with a user by sending documents to and receiving documents from a device that is used by the user. For example, a computer can send webpages to a web browser on a user's client device in response to requests received from the web browser.

A computer system can include a single computing device, or multiple computers that operate in proximity or generally remote from each other and typically interact through a communication network. Examples of communication networks include a local area network ("LAN") and a wide area network ("WAN"), an inter-network (for example, the Internet), a network including a satellite link, and peer-to-peer networks (for example, ad hoc peer-to-peer networks). A relationship of client and server can arise by virtue of computer programs running on the respective computers and having a client-server relationship to each other.

Figure 7:
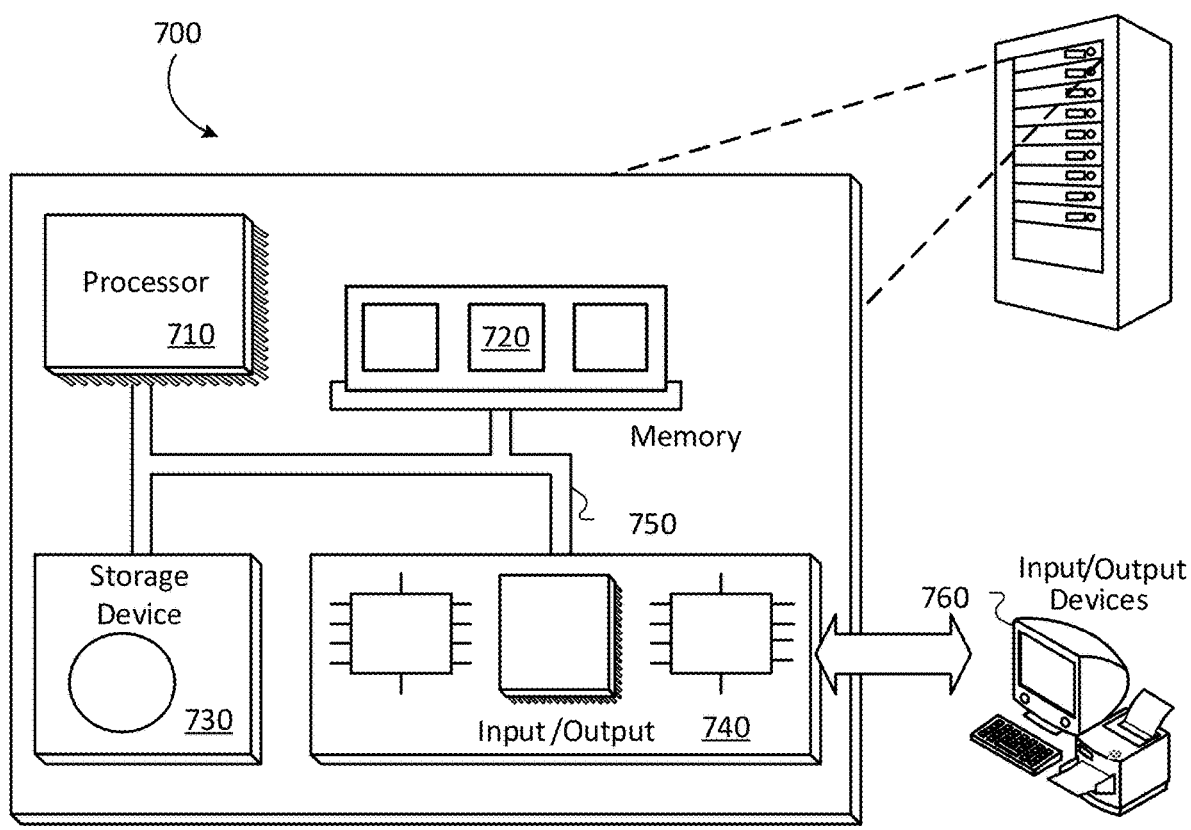
FIG. 7 is a schematic diagram of an example computer system.

FIG. 7 shows an example computer system 700 that includes a processor 710, a memory 720, a storage device 730 and an input/output device 740. Each of the components 710, 720, 730 and 740 can be interconnected, for example, by a system bus 750. The processor 710 is capable of processing instructions for execution within the system 700. In some implementations, the processor 710 is a single-threaded processor, a multi-threaded processor, or another type of processor. The processor 710 is capable of processing instructions stored in the memory 720 or on the storage device 730. The memory 720 and the storage device 730 can store information within the system 700.

The input/output device 740 provides input/output operations for the system 700. In some implementations, the input/output device 740 can include one or more of a network interface device, for example, an Ethernet card, a serial communication device, for example, an RS-232 port, or a wireless interface device, for example, an 802.11 card, a 3G wireless modem, a 4G wireless modem, or a 5G wireless modem, or both. In some implementations, the input/output device can include driver devices configured to receive input data and send output data to other input/output devices, for example, keyboard, printer and display devices 760. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, various modifications can be made without departing from the spirit and scope of the invention. Accordingly, other embodiments are within the scope of the claims.

What is claimed is:

1. A method comprising:
   obtaining, using one or more processors, a plurality of sets of training data, wherein each of the plurality of sets of training data comprises first data indicating a plurality of first properties of a plurality of first gas flow lines, wherein the plurality of first properties comprise, for each of the first gas flow lines:
   data representing a flow rate of a gas through that first gas flow line during a respective observation period,
   data representing a pressure of the gas in that first gas flow line during the observation period,
   data representing a first additive included in the gas in that first gas flow line during the observation period, wherein the first additive comprises a substance for inhibiting corrosion in that first gas flow line, and
   data representing whether that first gas flow line became corroded subsequent to the observation period;
   training, using the one or more processors, a computerized neural network based on the plurality of sets of training data;

obtaining, using one or more processors, second data indicating a plurality of second properties of a plurality of second gas flow lines, wherein the plurality of second properties comprise, for each of the plurality of second gas flow lines:
  data representing a flow rate of a gas through that second gas flow line,
  data representing a pressure of the gas in that second gas flow line, and
  data representing a second additive included in the gas in that second gas flow line, wherein the second additive comprises a substance for inhibiting corrosion in that second gas flow line;
for each of the plurality of second gas flow lines:
  determining, using the one or more processors and the computerized neural network, a first metric representing a risk of corrosion associated with that second gas flow line based on the second properties of that second gas flow line,
  determining, using the one or more processors, whether the first metric for that second gas flow line is greater than a threshold level, and
  responsive to determining that the first metric for that second gas flow line is greater than the threshold level, generating, using the one or more processors, a notification indicating the first metric for that second gas flow line for presentation to a user to facilitate at least one of a repair or maintenance of that second gas flow line.

2. The method of claim 1, wherein the plurality of second properties comprise, for each of the plurality of second gas flow lines:
  a composition of the gas in that second gas flow line.

3. The method of claim 1, wherein the plurality of second properties comprise, for each of the plurality of second gas flow lines:
  a composition of that second gas flow line.

4. The method of claim 1, further comprising:
  determining that the second data comprises incomplete data regarding one or more of the plurality of second gas flow lines, and
  in response to determining that the second data comprises incomplete data regarding the one or more of the plurality of second gas flow lines, modifying the second data to include additional data regarding the one or more of the plurality of second gas flow lines.

5. The method of claim 1, further comprising:
  determining that the second data comprises inaccurate data regarding one or more of the plurality of second gas flow lines, and
  in response to determining that the second data comprises inaccurate data regarding the one or more of the plurality of second gas flow lines, modifying the second data to correct the inaccurate data regarding the one or more of the plurality of second gas flow lines.

6. The method of claim 1,
  wherein the plurality of first properties comprise, for each of the plurality of first gas flow lines:
    data representing an extent of corrosion in that first gas line.

7. The method of claim 1, further comprising:
  for each of the plurality of second gas flow lines, determining a degree of severity of the risk of corrosion associated with that second gas flow line.

8. The method of claim 7, wherein the plurality of second gas flow lines comprise one or more hydrocarbon gas flow lines.

9. A system comprising:
one or more processors; and
one or more non-transitory computer readable media storing instructions that, when executed by the one or more processors, cause the one or more processors to perform operations comprising:
  obtaining a plurality of sets of training data, wherein each of the plurality of sets of training data comprises first data indicating a plurality of first properties of a plurality of first gas flow lines, wherein the plurality of first properties comprise, for each of the first gas flow lines:
    data representing a flow rate of a gas through that first gas flow line during a respective observation period,
    data representing a pressure of the gas in that first gas flow line during the observation period,
    data representing a first additive included in the gas in that first gas flow line during the observation period, wherein the first additive comprises a substance for inhibiting corrosion in that first gas flow line, and
    data representing whether that first gas flow line became corroded subsequent to the observation period;
  training a computerized neural network based on the plurality of sets of training data:
  obtaining second data indicating a plurality of second properties of a plurality of second gas flow lines, wherein the plurality of second properties comprise, for each of the plurality of second gas flow lines:
    data representing a flow rate of a gas through that second gas flow line,
    data representing a pressure of the gas in that second gas flow line, and
    data representing a second additive included in the gas in that second gas flow line, wherein the additive comprises a substance for inhibiting corrosion in that second gas flow line; and
  for each of the plurality of second gas flow lines:
    determining, using the computerized neural network, a first metric representing a risk of corrosion associated with that second gas flow line based on the second properties of that second gas flow line,
    determining whether the first metric for that second gas flow line is greater than a threshold level, and
    responsive to determining that the first metric for that second gas flow line is greater than the threshold level, generating a notification indicating the first metric for that second gas flow line for presentation to a user to facilitate at least one of a repair or maintenance of that second gas flow line.

10. The system of claim 9, wherein the plurality of second properties comprise, for each of the plurality of second gas flow lines:
  a composition of the gas in that second gas flow line.

11. The system of claim 9, wherein the plurality of second properties comprise, for each of the plurality of second gas flow lines:
  a composition of that second gas flow line.

12. The system of claim 9, the operations further comprising:
  determining that the second data comprises incomplete data regarding one or more of the plurality of second gas flow lines, and
  in response to determining that the second data comprises incomplete data regarding the one or more of the plurality of second gas flow lines, modifying the second data to include additional data regarding the one or more of the plurality of second gas flow lines.

13. The system of claim 9, further comprising:
determining that the second data comprises inaccurate data regarding one or more of the plurality of second gas flow lines, and
in response to determining that the second data comprises inaccurate data regarding the one or more of the plurality of second gas flow lines, modifying the second data to correct the inaccurate data regarding the one or more of the plurality of second gas flow lines.

14. The system of claim 9,
wherein the plurality of first properties comprise, for each of the plurality of first gas flow lines:
data representing an extent of corrosion in that first gas line.

15. The system of claim 9, the operations further comprising:
for each of the plurality of second gas flow lines, determining a degree of severity of the risk of corrosion associated with that second gas flow line.

16. The system of claim 15, wherein the plurality of second gas flow lines comprise one or more hydrocarbon gas flow lines.

17. One or more non-transitory computer readable media storing instructions that, when executed by one or more processors, cause the one or more processors to perform operations comprising:
obtaining a plurality of sets of training data, wherein each of the plurality of sets of training data comprises first data indicating a plurality of first properties of a plurality of first gas flow lines, wherein the plurality of first properties comprise, for each of the first gas flow lines:
data representing a flow rate of a gas through that first gas flow line during a respective observation period,
data representing a pressure of the gas in that first gas flow line during the observation period,
data representing a first additive included in the gas in that first gas flow line during the observation period, wherein the first additive comprises a substance for inhibiting corrosion in that first gas flow line, and
data representing whether that first gas flow line became corroded subsequent to the observation period;
training a computerized neural network based on the plurality of sets of training data;
obtaining second data indicating a plurality of second properties of a plurality of second gas flow lines, wherein the plurality of second properties comprise, for each of the plurality of second gas flow lines:
data representing a flow rate of a gas through that second gas flow line,
data representing a pressure of the gas in that second gas flow line, and
data representing a second additive included in the gas in that second gas flow line, wherein the additive comprises a substance for inhibiting corrosion in that second gas flow line; and
for each of the plurality of second gas flow lines:
determining, using the computerized neural network, a first metric representing a risk of corrosion associated with that second gas flow line based on the second properties of that second gas flow line,
determining whether the first metric for that second gas flow line is greater than a threshold level, and
responsive to determining that the first metric for that second gas flow line is greater than the threshold level, generating a notification indicating the first metric for that second gas flow line for presentation to a user to facilitate at least one of a repair or maintenance of that second gas flow line.

* * * * *

UNITED STATES PATENT AND TRADEMARK OFFICE
CERTIFICATE OF CORRECTION

| | | |
|---|---|---|
| PATENT NO. | : 12,038,423 B2 | Page 1 of 1 |
| APPLICATION NO. | : 17/409400 | |
| DATED | : July 16, 2024 | |
| INVENTOR(S) | : Muhammad Sohaib Khan et al. | |

It is certified that error appears in the above-identified patent and that said Letters Patent is hereby corrected as shown below:

In the Claims

Column 22, Line 27, Claim 9, please replace "data:" with -- data; --.

Signed and Sealed this
First Day of October, 2024

Katherine Kelly Vidal
*Director of the United States Patent and Trademark Office*